(12) United States Patent
Poulsen

(10) Patent No.: US 10,241,350 B1
(45) Date of Patent: Mar. 26, 2019

(54) MAPPING A CENTRAL VISUAL FIELD ONTO A PERIPHERAL VISUAL SENSOR

(71) Applicant: Peter Davis Poulsen, Grants Pass, OR (US)

(72) Inventor: Peter Davis Poulsen, Grants Pass, OR (US)

(*) Notice: Subject to any disclaimer, the term of this patent is extended or adjusted under 35 U.S.C. 154(b) by 325 days.

(21) Appl. No.: 15/203,762

(22) Filed: Jul. 6, 2016

Related U.S. Application Data

(60) Provisional application No. 62/231,424, filed on Jul. 6, 2015.

(51) Int. Cl.
| | | |
|---|---|---|
| G02C 7/14 | (2006.01) | |
| G02B 27/00 | (2006.01) | |
| G02B 27/01 | (2006.01) | |

(52) U.S. Cl.
CPC ............ *G02C 7/14* (2013.01); *G02B 27/0093* (2013.01); *G02B 27/0172* (2013.01); *G02B 2027/0178* (2013.01); *G02C 2202/10* (2013.01); *G02C 2202/20* (2013.01)

(58) Field of Classification Search
None
See application file for complete search history.

(56) References Cited

U.S. PATENT DOCUMENTS

| | | | | |
|---|---|---|---|---|
| 4,772,113 A | * | 9/1988 | Parker | G02C 7/06 351/159.45 |
| 4,958,924 A | * | 9/1990 | Parker | G02C 7/06 351/159.45 |
| 5,274,405 A | * | 12/1993 | Webster | A61B 3/032 351/158 |
| 5,327,191 A | * | 7/1994 | Shindo | G03B 13/36 396/51 |
| 5,543,816 A | * | 8/1996 | Heacock | G02B 13/18 345/8 |
| 7,311,401 B2 | * | 12/2007 | Goldfain | A61B 3/156 351/200 |
| 8,956,396 B1 | * | 2/2015 | Friend | A61N 5/0622 607/88 |
| 2002/0036750 A1 | * | 3/2002 | Eberl | A61B 3/12 351/207 |
| 2010/0149073 A1 | * | 6/2010 | Chaum | G02B 27/0093 345/8 |

\* cited by examiner

*Primary Examiner* — David D Davis
(74) *Attorney, Agent, or Firm* — David S. Alavi

(57) ABSTRACT

One or more peripheral optical elements direct light emanating from a central field portion of a visual field (via one or more central optical elements of a visual sensor) onto a peripheral sensor portion of the visual sensor. The peripheral optical element(s) map an image of the central field portion onto the peripheral sensor portion for detection by the visual sensor. The central optical element(s) define the central field portion and form (from light emanating from the central field portion and directly incident on the central optical element(s)) an image of the central field portion on a corresponding central sensor portion of the visual sensor distinct from the peripheral sensor portion.

25 Claims, 10 Drawing Sheets

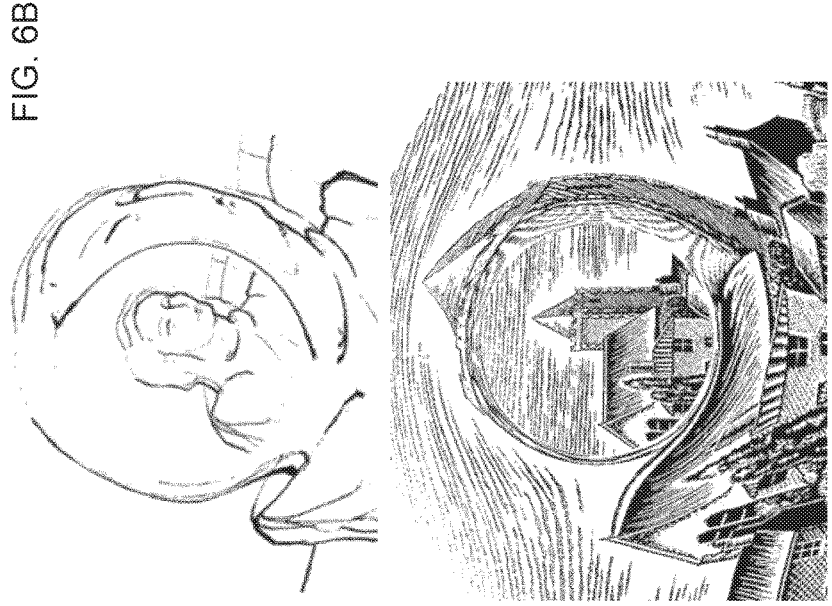
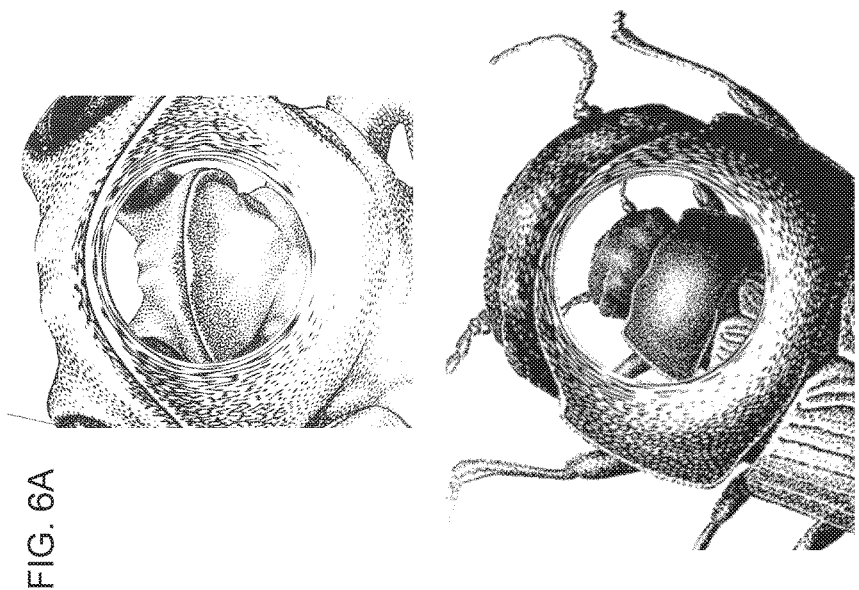
FIG. 6A  FIG. 6B  FIG. 6C  FIG. 6D

MAPPING A CENTRAL VISUAL FIELD ONTO A PERIPHERAL VISUAL SENSOR

BENEFIT CLAIMS TO RELATED APPLICATIONS

This application claims benefit of U.S. provisional App. No. 62/231,424 entitled "Cross-sensory augmentation system" filed Jul. 6, 2015 in the name of Peter Davis Poulsen, said provisional application being incorporated by reference as if fully set forth herein.

FIELD OF THE INVENTION

The field of the present invention relates to vision enhancement or assistance. In particular, apparatus and methods are disclosed for mapping an image of a central visual field onto a peripheral portion of a visual sensor.

BACKGROUND

FIG. 1 is a schematic illustration of nominal divisions or categorizations of the angular field of view of a human eye. The highest concentration of photoreceptor cells in the retina is in the region of the macula, and more particularly within the subregion of the macula called the fovea. The central optical elements of the eye, i.e., the cornea and the lens, together with the macula define a macular visual field 107 that typically spans an angle of about 18° to 19°; the macular visual field is considered the center of the overall visual field. Note that the depiction in FIG. 1 is a two-dimensional representation of a three-dimensional visual field. The macular visual field therefore corresponds roughly to a cone with an included angle of about 18°. Other two-dimensional depictions included in the present disclosure shall be similarly interpreted as representing three-dimensional, often roughly conical arrangements as appropriate. The macular angular region 107 can be sub-divided into roughly concentric regions: the fovea (the central, inner region of the macula with a corresponding field of view having an included angle of about 5° and defining the center of the visual field), which is embedded within the parafovea (with a corresponding ring-like field of view between about 2.5° and about 4° from the center of the visual field), which in turn is embedded in the perifovea (with a corresponding ring-like field of view between about 4° and about 9° from the center of the visual field). The roughly 18° macular angular field 107 corresponds to a macular region 108 on the retina 109 (FIG. 3) that is about 5.5 mm across. The macular region 108 typically is considered the central retina portion in the present disclosure, while the rest of the retina 109 is considered the peripheral retina portion; a different definition of the central and peripheral retina portions can be employed if suitable, desirable, or necessary. For example, in some examples only the fovea is considered the central retina portion while the remainder of the retina (including the parafovea and perifovea) is considered the peripheral retina portion; in other examples the fovea and parafovea together are considered the central retina portion while the remainder of the retina (including the perifovea) is considered the peripheral retina portion.

Referring again to FIG. 1, the periphery 90 of the visual field extends between about 9° and about 100° to 110° from the center of the visual field. The peripheral field portion 90 can be subdivided into the near periphery 90a (between about 9° and about 30° from center), the mid periphery 90b (between about 30° and about 60°), and the far periphery 90c (between about 60° and about 100° to 110°). Those subdivision are arbitrary and are provided only for convenience of description.

FIG. 2 is an example of photoreceptor density as a function of view angle for rod photoreceptors (curve 118) and cone photoreceptors (curve 119) in a human retina. The minimum in rod density that coincides with the maximum cone density corresponds roughly to the location of the fovea on the retina 109. The other minimum in the rod density corresponds to the so-called blind spot, where the optic nerve enters the retina. Each curve in FIG. 2 represents a specific cross section across the eye; a different cross section might miss the blind spot so that the curve 118 would exhibit only a single minimum in the rod density curve 118. An alternative definition of the central and peripheral retina portions can be based on relative densities of rods versus cones. That portion of the retina having a cone-to-rod ratio sufficiently high would be considered the central retina portion, and the rest of the retina (with a lower ratio) would be considered the peripheral retina portion. Note that the alternative definitions (macula-based or rod/cone-based) typically nearly coincide.

The macula (and the fovea in particular) has the highest photoreceptor density and provides the sharpest vision at the center of the visual field. Central vision typically is provided primarily by cones; peripheral vision is provided primarily by rods. It has long been observed and well understood that cones provide color vision and high visual acuity under relatively high levels of illumination, while rods provide more sensitivity at relatively low levels of illumination. Ganglia present in the peripheral retina portion also provide enhanced sensitivity to detecting the presence or direction of motion.

A leading cause of vision loss is macular degeneration, with incidence rates estimated to be as high as 1.5% among people over 40 years old. The central portion of the retina 109, i.e., the macula 108, deteriorates leading to blurred or no vision in the center of the visual field. Loss of central vision can make it hard to recognize faces, drive, read, or perform other activities of daily life. Peripheral vision typically is unaffected.

SUMMARY

An optical apparatus comprises a set of one or more peripheral optical elements. At least a portion of light emanating from a central field portion of a visual field is directed (via a set of one or more central optical elements of a visual sensor) by the one or more peripheral optical elements onto a peripheral sensor portion of the visual sensor. The one or more peripheral optical elements map at least a partial image of the central field portion onto the peripheral sensor portion for detection by the visual sensor. The one or more central optical elements are arranged so as to define the central field portion and to form at least a partial image of the central field portion on a corresponding central sensor portion of the visual sensor that is distinct from the peripheral sensor portion. That image is formed from at least a portion of light emanating from the central field portion that would be directly incident on the one or more central optical elements (e.g., if not obstructed by one or more of the peripheral optical elements).

A method comprises directing, using the one or more peripheral optical elements, onto the peripheral sensor portion via the one or more central optical elements, at least a portion of light emanating from the central field portion so as to map at least a partial image of the central field portion onto the peripheral sensor portion for detection by the visual sensor.

Objects and advantages pertaining to visual imaging and detection may become apparent upon referring to the example embodiments illustrated in the drawings and disclosed in the following written description or appended claims.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIGS. 6A through 6D are examples of respective central visual field portions images onto corresponding central retinal portions and mapped onto corresponding peripheral retina portions.

The embodiments depicted are shown only schematically: all features may not be shown in full detail or in proper proportion, certain features or structures may be exaggerated relative to others for clarity, and the drawings should not be regarded as being to scale. For example, the sets of peripheral optical elements depicted as including only a few elements (e.g., as in FIGS. 8 and 9) might actually include dozens, or even hundreds of individual elements. In addition, the height, depth, or width of optical elements or other features can be exaggerated relative to, e.g., the thickness of an underlying substrate or the distance between the eye and the optical elements. The embodiments shown are only examples: they should not be construed as limiting the scope of the present disclosure or appended claims.

DETAILED DESCRIPTION OF EMBODIMENTS

It would be desirable to enhance sensory input provided by the peripheral retina portion of the eye. Such enhancement can at least partly compensate for effects of macular degeneration, or can be advantageous in the context of, e.g., hunting, combat training or maneuvers, or nighttime activities.

Figure 1:
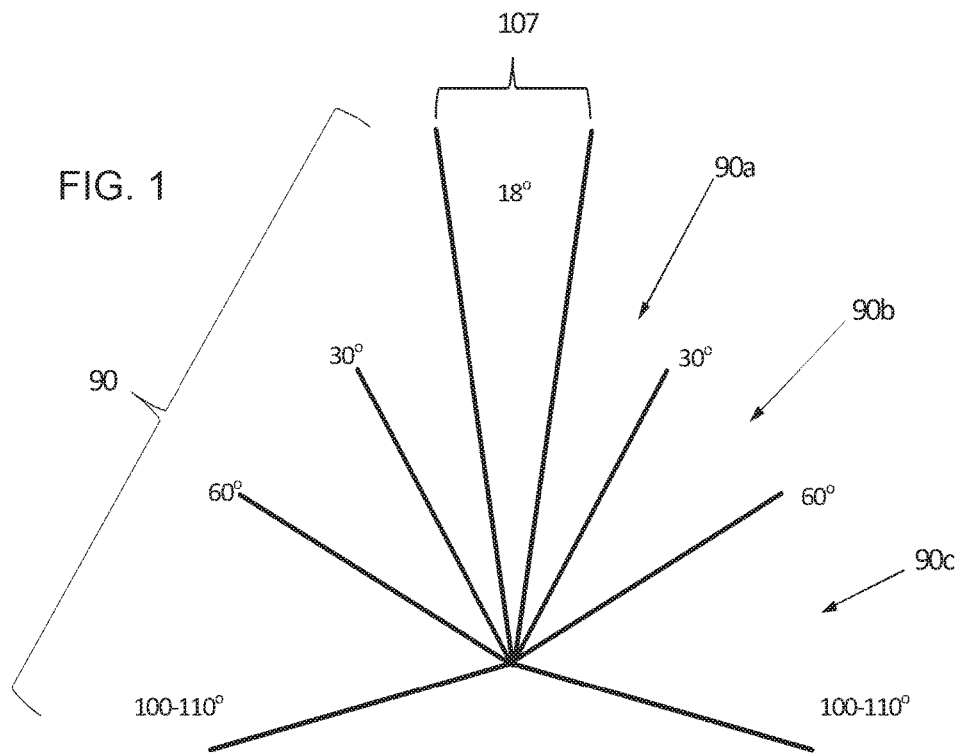
FIG. 1 illustrates schematically nominal divisions or categorizations of the angular field-of-view of the human eye.
Figure 2:
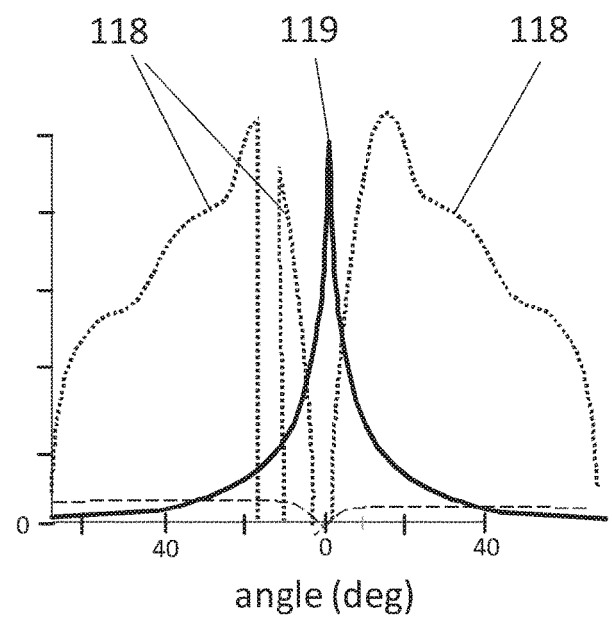
FIG. 2 is an example of photoreceptor density as a function of view angle for rods and cones in a human retina.
Figure 3:
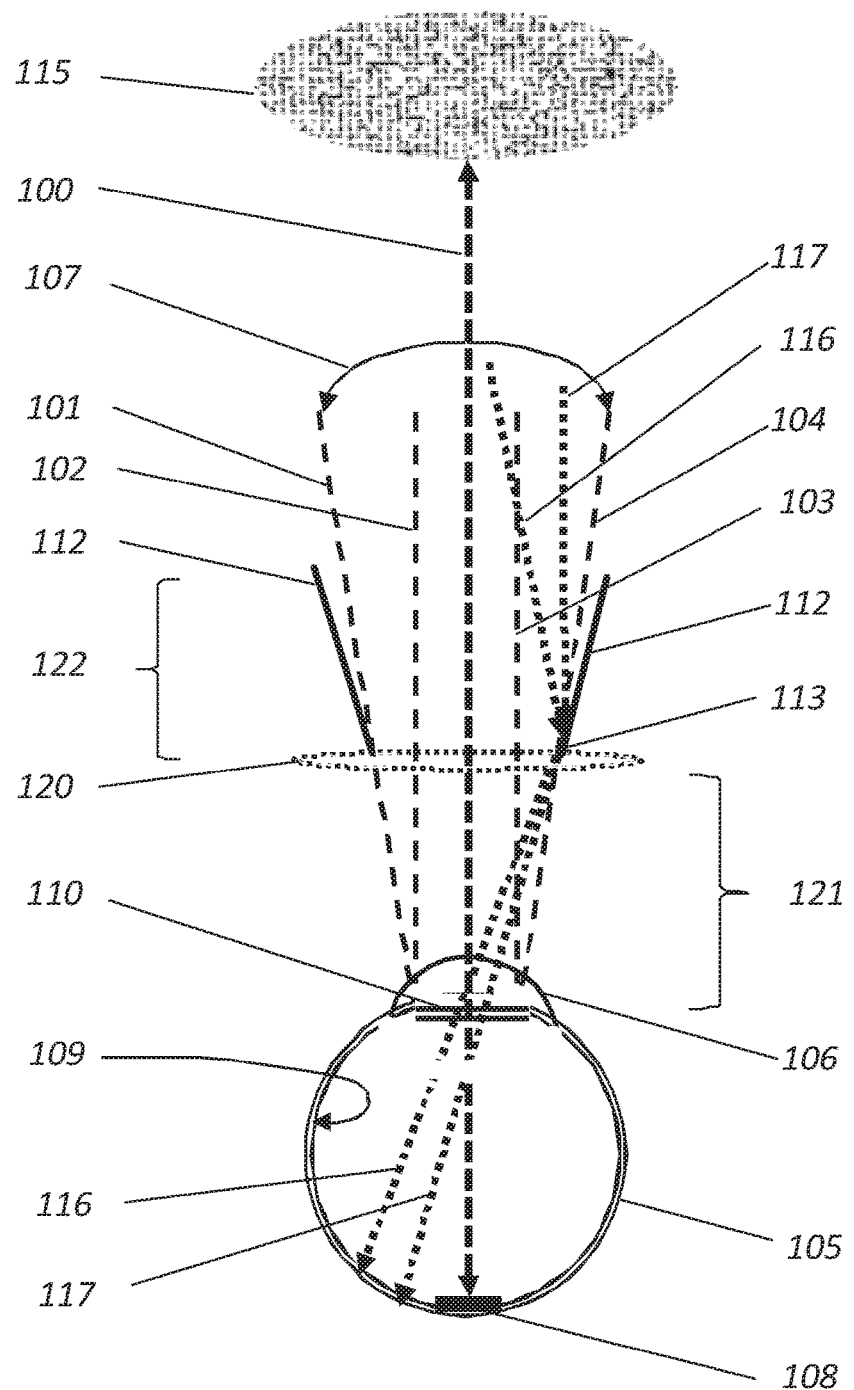
FIG. 3 illustrates schematically an example of a radial mapping of a central visual field portion onto a peripheral retina portion using peripheral optical elements.
Figure 4:
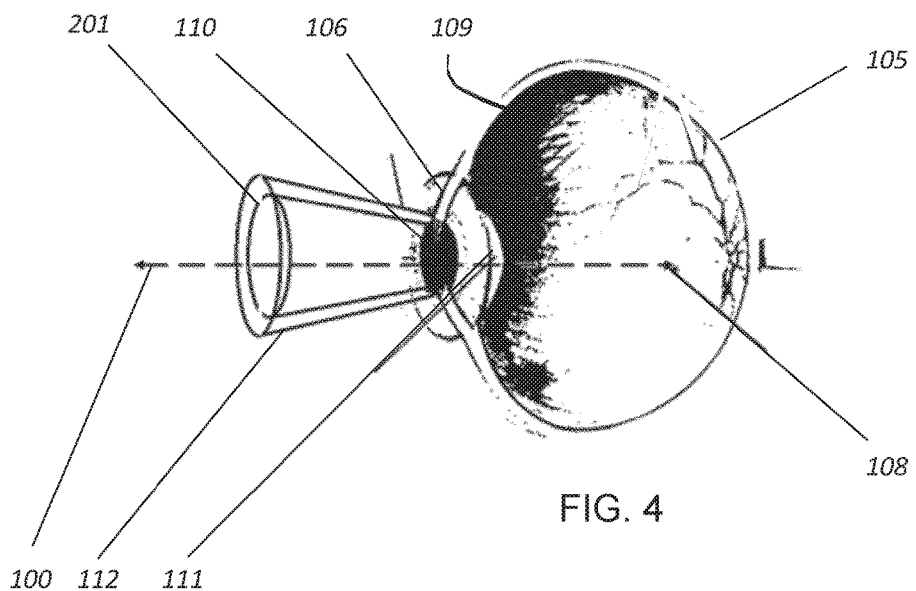
FIG. 4 illustrates schematically a frusto-conical reflector surface relative to a macular field or view.
Figure 7:
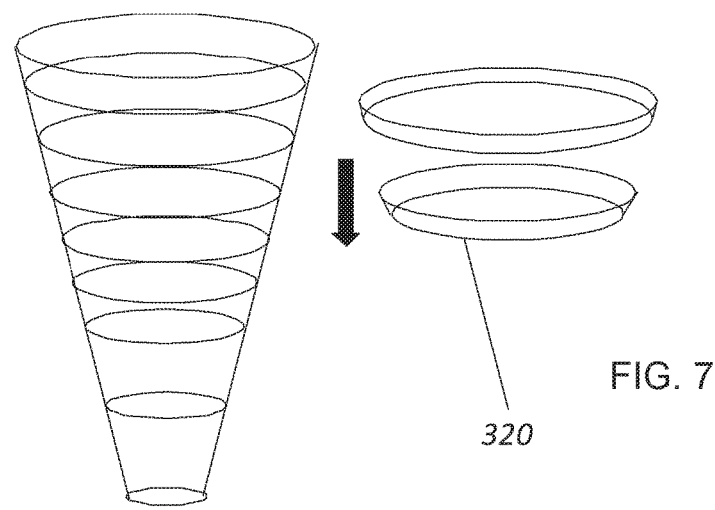
FIG. 7 illustrates schematically a single frusto-conical reflector divided into a set of multiple nested frusto-conical reflector segments.
Figure 8:
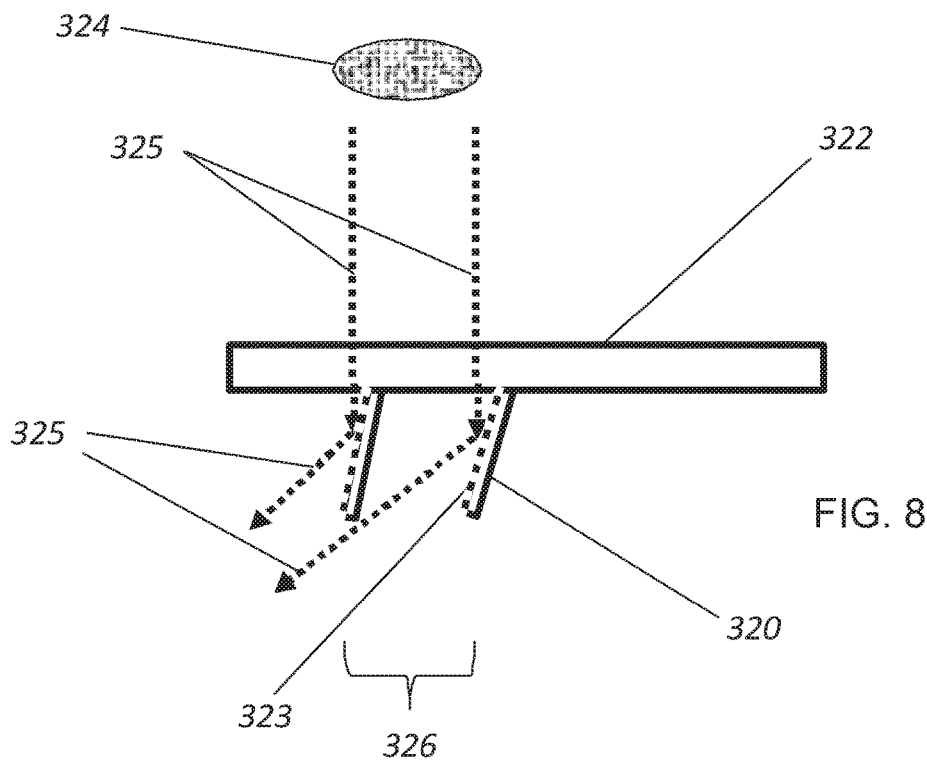
FIG. 8 illustrates schematically two reflective peripheral optical elements.
Figure 9:
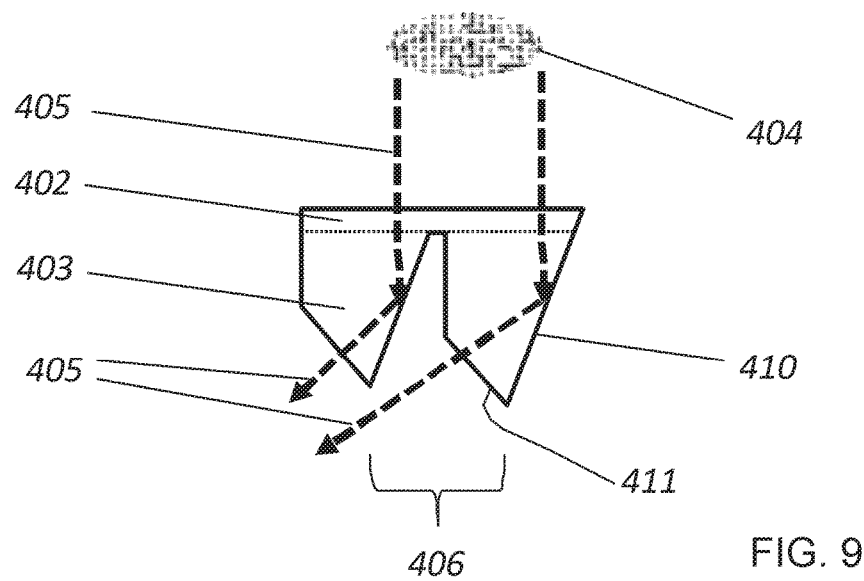
FIG. 9 illustrates schematically two refractive and reflective peripheral optical elements.
Figure 10:
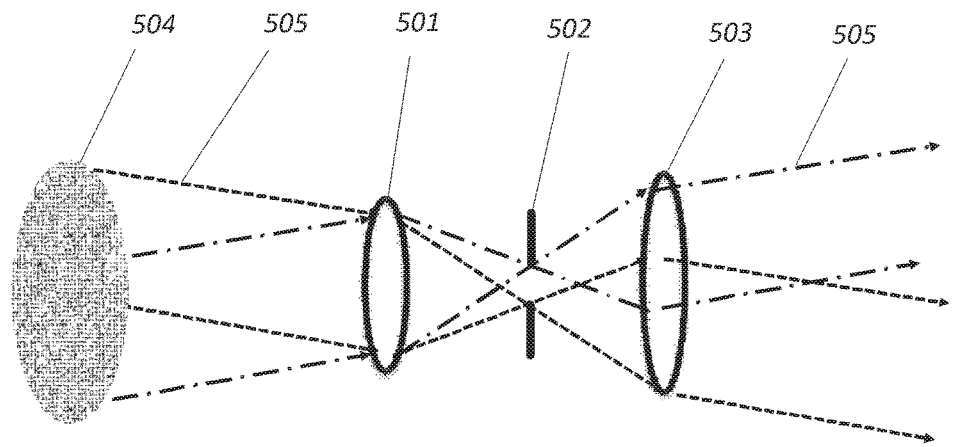
FIG. 10 illustrates schematically a set of peripheral optical elements that includes one or more focusing optical elements and one or more apertures.
Figure 11:
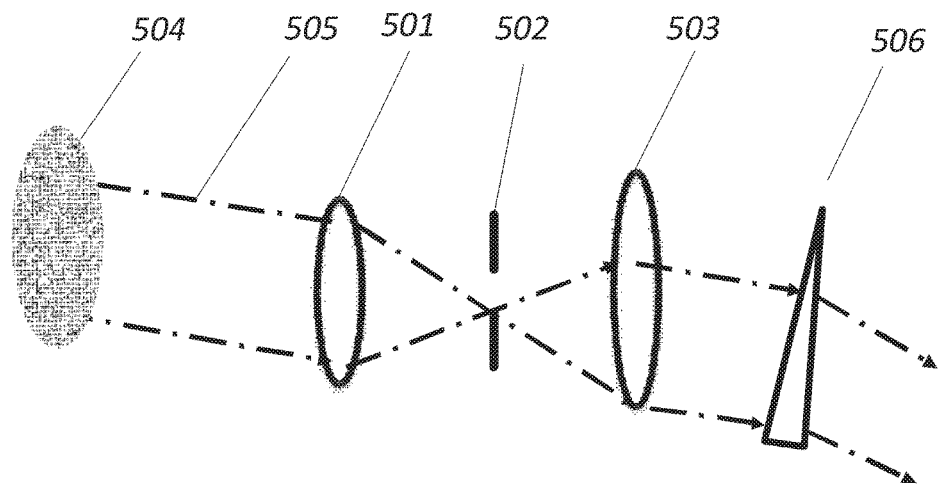
FIG. 11 illustrates schematically a set of peripheral optical elements that includes one or more focusing optical elements, one or more apertures, and one or more refractive optical elements.
Figure 12:
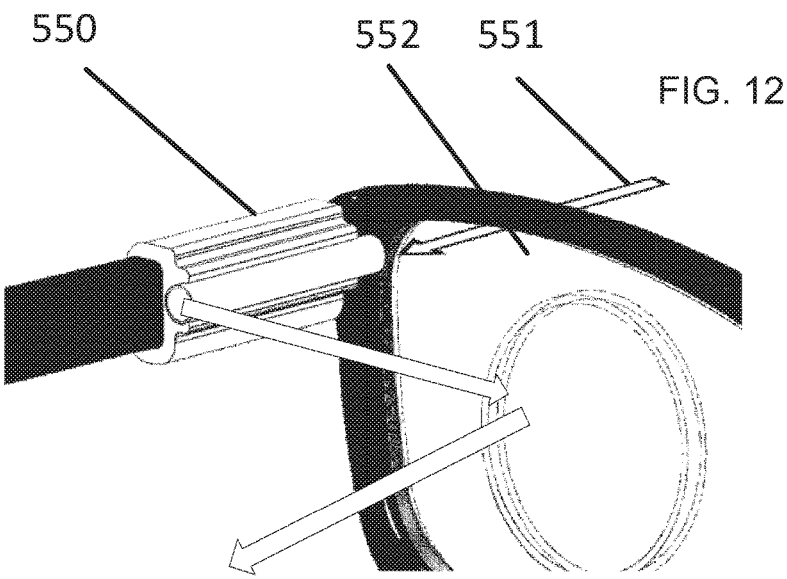
FIG. 12 illustrates schematically a set of peripheral optical elements mounted on or incorporated into a set of eyewear, e.g., a pair of eyeglasses.
Figure 15:
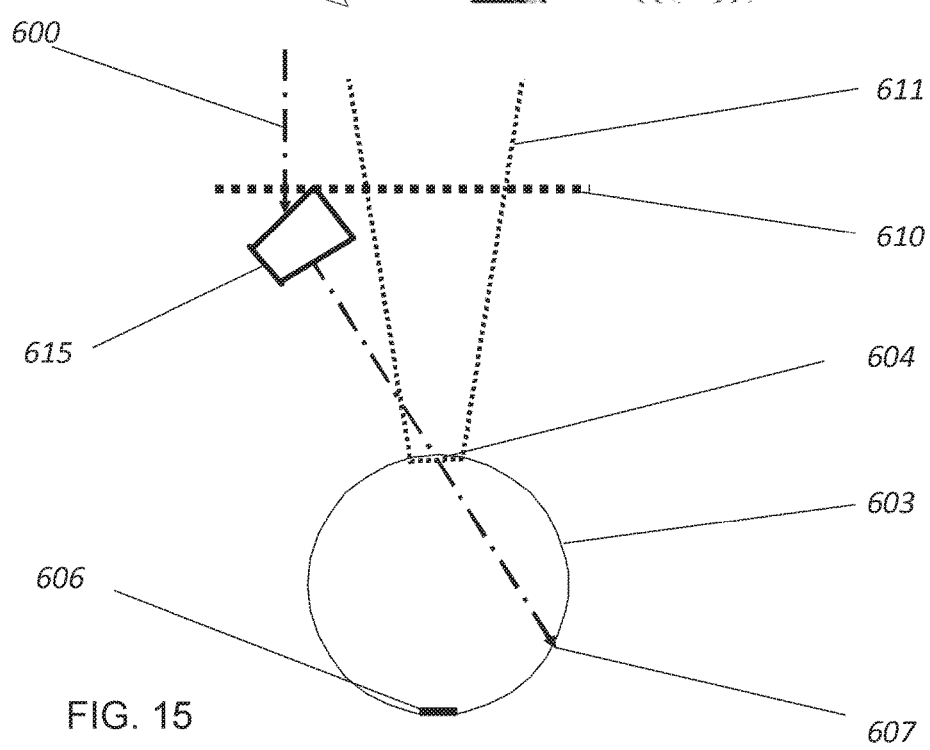
FIG. 15 illustrates schematically an example of a set of peripheral optical elements that includes one or more annular prisms.
Figure 13:
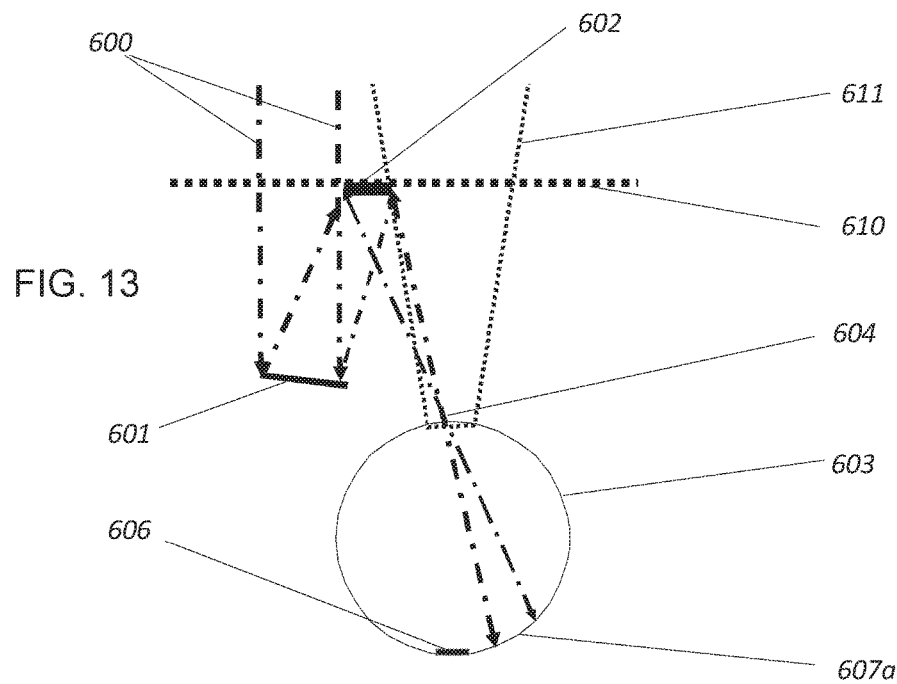
FIGS. 13 and 14 illustrate schematically respective examples of peripheral optical elements that include one or more annular reflectors.
Figure 14:
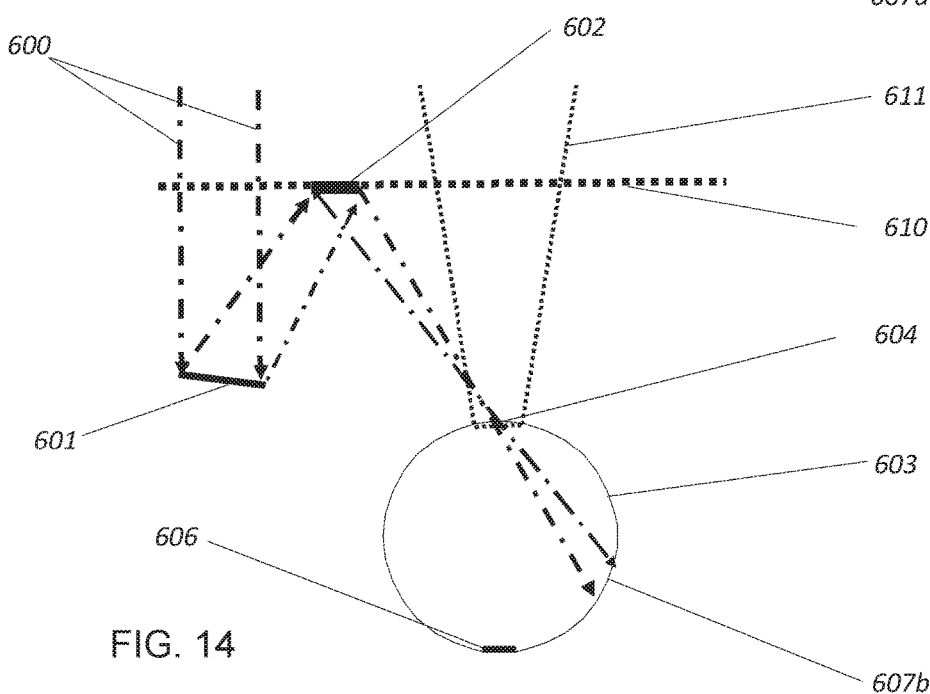
Figure 16:
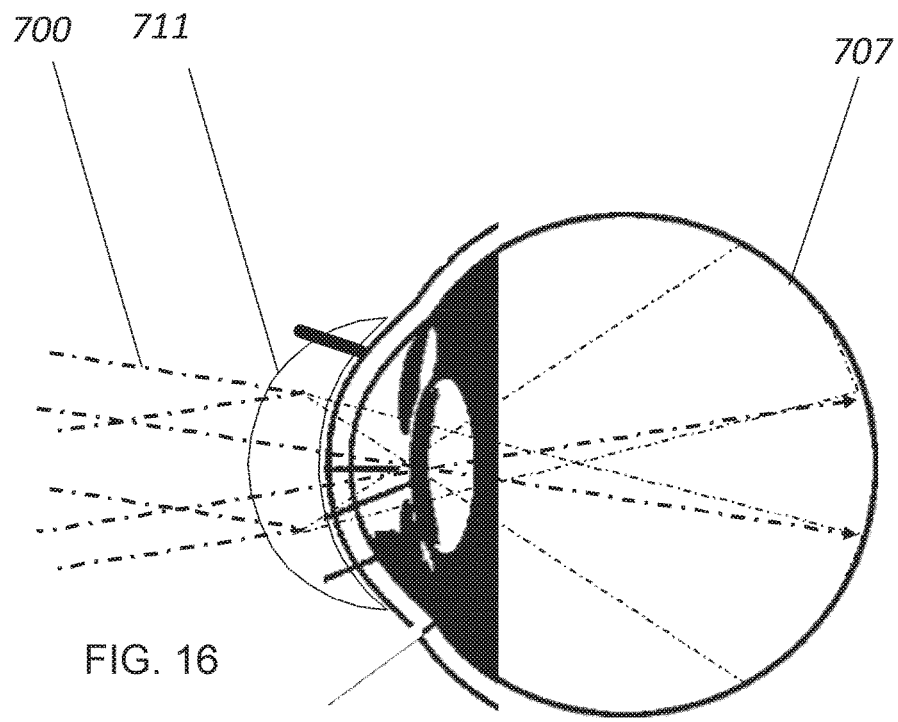
FIG. 16 illustrates schematically an example of a set of peripheral optical elements incorporated into a contact lens.

That result is achieve by an inventive optical apparatus comprising a set of one or more peripheral optical elements (e.g., conical mirror 112 in FIGS. 3 and 4; mirror segments 320 in FIG. 7; reflectors 320/323 in FIG. 8; reflective/refractive surfaces 410/411 in FIG. 9; lenses 501/503 and aperture 502 in FIGS. 10 and 11; optical arrangement 550 in FIG. 12; mirrors 601/602 in FIGS. 13 and 14; prism 615 in FIG. 15; incorporated into contact lens 711 in FIG. 16). The peripheral optical elements are arranged so as to direct light emanating from a central portion of the visual field onto a peripheral sensor portion (e.g., the peripheral retina portion) of a visual sensor (e.g., the retina of a human eye). The central field portion is labelled as element 115 in FIG. 3, as element 324 in FIG. 8, as element 404 in FIG. 9, and as element 504 in FIGS. 10 and 11. The light emanating from the central field portion and then directed by the peripheral optical elements is labelled as rays 116/117 in FIG. 3, as rays 325 in FIG. 8, as rays 405 in FIG. 9, as rays 505 in FIGS. 10 and 11, as rays 600 in FIGS. 13 through 15, and rays 700 in FIG. 16. The peripheral sensor portion (e.g., the peripheral retina portion) is labelled as element 109 in FIG. 3, as elements 607/607a/607b in FIGS. 13 through 15, and as element 707 in FIG. 16. The light directed by the peripheral optical elements from the central field portion to the peripheral sensor portion is directed also via a set of one or more central optical elements of the visual sensor. If the visual sensor is a human eye (as is the case in the examples shown; labelled as element 105 in FIGS. 3 and 4 and as element 603 in FIGS. 13 through 15), then the central optical elements include the cornea and lens of the eye, the central sensor portion is the central retina portion (e.g., the fovea in some examples; the fovea and parafovea in some examples; the macula in some examples, labelled as element 108 in FIG. 3 and as element 606 in FIGS. 13 through 15), and the peripheral sensor portion is the peripheral retina portion (i.e., that portion of the retina not included in the central retina portion); the central and peripheral retina portions are distinct areas of the retina.

While the disclosed examples all include a human eye as the visual sensor, the inventive apparatus can be employed with other visual sensors, e.g., with a set of one or more imaging optics forming an image, e.g., on a CCD, CMOS, or other imaging array detector, or on photographic plate or film. The terms "central sensor portion" and "peripheral sensor portion" are used in the present description somewhat interchangeably with the corresponding terms "central retina portion" and "peripheral retina portion," respectively, and should be understood as designating the corresponding retina portions when indicated by context, but can apply to other types of sensors as appropriate. The central and peripheral sensor portions are distinct areas of the visual sensor.

The central sensor portion and the central optical elements are arranged so as to define the central portion of the visual field; the central optical elements are arranged to form, from at least a portion of light emanating from the central field portion, at least a partial image of the central field portion on a corresponding central sensor portion of the visual sensor that is distinct from the peripheral sensor portion. Light forming that central image would be directly incident on the one or more central optical elements, unless blocked in some cases by one or more of the peripheral optical elements. Referring to FIG. 3, the rays 101/102/103/104 emanate from the central field portion 115, are focused by the cornea 106 and lens of the eye 105, and form an image on the macula 108 of the retina of the eye 105. The outer rays 101/104 roughly define the outer limits of the macular field of view; rotated into three dimensions, the macular field of view corresponds roughly to cone 201 (FIG. 4) or 611 (FIGS. 13 through 15).

To make use of the peripheral sensor portion, at least a portion of light emanating from the central field portion is directed onto the peripheral sensor portion so as to map at least a partial image of the central field portion onto the peripheral sensor portion for detection. In some instances, light emanating from the central field portion forms both the image on the central sensor portion (e.g., rays 101/102/103/104 in FIG. 3) and the mapping of the image on the peripheral sensor portion (e.g., rays 116/117 in FIG. 3). In other instances, the peripheral optical elements can substantially entirely prevent light from the central field portion from reaching the central sensor portion and forming an image there. Numerous arrangements of one or more peripheral optical elements can be employed to achieve either of those results. Some examples are described further below.

The peripheral optical elements can be arranged in any suitable way to define a corresponding peripheral sensor portion. In examples wherein the visual sensor is a human eye of a user, including a cornea, lens, and retina, the central sensor portion includes a central retina portion of the retina, the peripheral sensor portion includes a peripheral retina portion of the retina that surrounds the central retina portion, and the set of one or more central optical elements includes the cornea and the lens; in some instances the central optical elements can also include one or more corrective lenses (e.g., eyeglasses, contact lens, or lens implant). In some examples the peripheral optical elements are arranged so that the central retina portion includes predominantly cone photoreceptors and the peripheral retina portion includes predominantly rod photoreceptors. In some examples the peripheral optical elements are arranged so that the central retina portion includes only a macular portion of the retina; in some examples the peripheral optical elements are arranged so that the central retina portion includes only parafoveal and foveal portions of the retina; in some examples the peripheral optical elements are arranged so that the central retina portion includes only the foveal portion of the retina. In many examples, the set of one or more peripheral optical elements is mounted on or incorporated into a set of eyewear; other suitable arrangements or hardware can be employed for arranging the peripheral optical elements relative to the eye or other visual sensor, e.g., a headset or head-mounted display.

Any suitable mapping of the central field portion onto the peripheral sensor portion can be employed. The mapping can, but need not, preserve the recognizability of the imaged central field portion to an untrained user; the mapping need only be well-defined and reproducible.

Figure 5A:
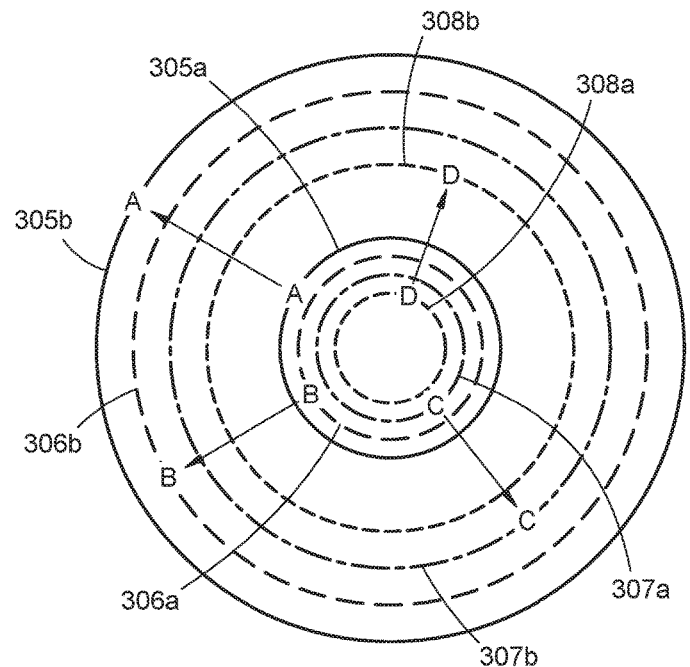
FIGS. 5A and 5B illustrate schematically non-inverted and inverted outward radial displacement mappings, respectively.

One example of a suitable mapping is a non-inverted outward radial displacement, which is illustrated schematically in FIG. 5A and in the examples of FIGS. 6A through 6D. The set of one or more peripheral optical elements is arranged so as to define an image-mapping center point; the center point typically, but not necessarily, at least roughly coincides with the center of the central sensor portion (e.g., the center retina portion). According to the non-inverted outward radial displacement, a corresponding portion of the light emanating from each mapped segment of the central field portion is directed by one or more of the peripheral optical elements onto a corresponding segment of the peripheral sensor portion that is displaced, radially outward away from the center point, relative to a corresponding segment of the central sensor portion where that mapped central field portion would be imaged. FIG. 5A illustrates this schematically. The mapping can optionally include magnification or demagnification, which need not be constant with respect to distance from the center point. The concentric circles 305a/306a/307a/308a represent the image of the central field portion on the central sensor portion, e.g., the image of the central field portion normally formed on the macula by the cornea and lens of the eye (and corrective lens, if any). The outermost circle 305a roughly corresponds to the outer boundary of the central sensor portion (e.g., the macula boundary in some examples, the parafoveal boundary in some examples, the foveal boundary in some examples, or a transition boundary determined by relative rod and cone densities, or other suitably determined boundary). The concentric circles 305b/306b/307b/308b represent the mapping according to the non-inverted outward radial displacement. The center of the central image is shifted outward to or beyond the boundary 305a but within the circle 308b; pixels of the central image on the circle 308a are shifted outward to the circle 308b; pixels of the central image on the circle 307a are shifted outward to the circle 307b; pixels of the central image on the circle 306a are shifted outward to the circle 306b; pixels of the central image on the circle 305a (outer edge of the central image) are shifted outward to the circle 305b (outer edge of the mapping). The letters A/B/C/D are not part of the image, but merely denote the corresponding positions and orientations of certain pixels in the central image and peripheral mapping for illustrative purposes. Note that each letter is shifted radially outward from its original position away from the center point, and that the relative distances from the center point remain in the same order (e.g., if A is farther off-center than B in the center image, then A is also farther off-center than B in the mapping). Examples of images mapped according to FIG. 5A are shown in FIGS. 6A through 6D. The information content of the central image is reproduced, in distorted but still recognizable form, in the peripheral mapping.

Figure 5B:
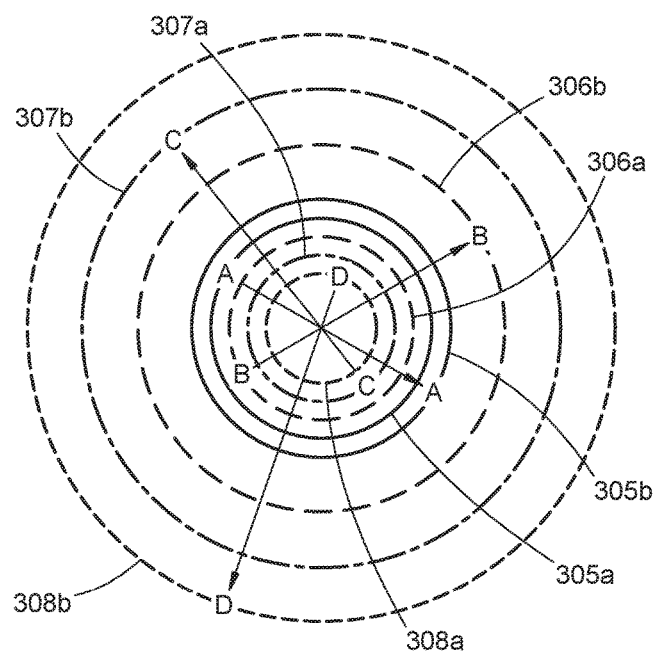

Another example of a suitable mapping is an inverted outward radial displacement relative to the center point, which is illustrated schematically in FIG. 5B. According to the inverted outward radial displacement, a corresponding portion of the light emanating from each mapped segment of the central field portion is directed by one or more of the peripheral optical elements onto a corresponding segment of the peripheral sensor portion that is displaced, radially outward across the center point, relative to a corresponding segment of the central sensor portion where that mapped central field portion would be imaged. FIG. 5B illustrates this schematically. The mapping can optionally include magnification or demagnification, which need not be constant with respect to distance from the center point. As before, the concentric circles 305a/306a/307a/308a represent the image of the central field portion on the central sensor portion, e.g., the image of the central field portion normally formed on the macula by the cornea and lens of the eye (and corrective lens, if any). The outermost circle 305a roughly corresponds to the outer boundary of the central sensor portion (e.g., the macula boundary in some examples, the parafoveal boundary in some examples, the foveal boundary in some examples, or a transition boundary determined by relative rod and cone densities, or other suitably determined boundary). The concentric circles 305b/306b/307b/308b represent the mapping according to the inverted outward radial displacement. The center of the central image is inverted and shifted outward beyond the circle 305a; pixels of the central image on the circle 308a are inverted and shifted outward to the circle 308b; pixels of the central image on the circle 307a are inverted and shifted outward to the circle 307b; pixels of the central image on the circle 306a are inverted and shifted outward to the circle 306b; pixels of the central image on the circle 305a (outer edge of the central image) are inverted and shifted outward to the circle 305b (inner edge of the mapping). The letters A/B/C/D are not part of the image, but merely denote the corresponding positions and orientations of certain pixels in the central image and peripheral mapping for illustrative purposes. Note that each letter is shifted radially outward from its original position across the center point, and that the relative distances from the center point are inverted (e.g., if A is farther off-center than B in the center image, then B is farther off-center than A in the mapping). In these examples the information content of the central image is reproduced, in distorted and not necessarily recognizable form, in the peripheral mapping.

In some examples the set of one or more peripheral optical elements includes a set of one or more reflective optical elements. The reflective optical elements can include front-surface reflectors (coated or uncoated), rear-surface reflectors (coated or uncoated), or internal reflectors (coated or uncoated). If rear-surface or internal reflectors are employed, one or more of them can include refraction at a material interface. The reflectors can be maximally reflecting or only partially reflecting. Partial reflectivity can be advantageous if, for example, it is desired that peripheral field portions be imaged onto the peripheral sensor portion, in addition to the mapped central image. In that way some normal peripheral vision can be maintained, even though the peripheral retina portion also is being used to receive visual information from the central field portion. In some instances, if partial reflectivity from an uncoated surface (i.e., Fresnel reflection) is sufficient, the expense of coated peripheral optical elements can be reduced or eliminated. In some examples the geometry of the visual sensor and the peripheral optical elements result in high (e.g., near-grazing) incidence angles, and Fresnel reflection from an uncoated peripheral optical element can be sufficient. Typical materials can include, e.g., glasses, plastics, or other suitable transparent materials (if rear-surface or internal reflection is employed). Any suitable reflective coating can be employed if needed or desired, including single-layer, multi-layer, metal, or dielectric coatings.

In the example of FIGS. 3 and 4, a frusto-conical reflector 112 (right or oblique; circular, elliptical, oval, or other suitable base shape; constant or varying cone angle) maps the central field portion 115 onto the peripheral retina portion according to an inverted outward radial displacement (indicated by the rays 116/117 crossing the centerline before reaching the peripheral retina portion). A frusto-pyramidal reflector (right or oblique; any suitable regular or irregular polygonal base shape; constant or varying slope angle) can be similarly employed. The included angle of the frusto-conical reflector 112 or frusto-pyramidal reflector typically exceeds the angular field of the central sensor portion (e.g., the macula or the fovea), as shown in FIG. 3 (reflector 112 relative to rays 101 and 104) and in FIG. 4 (reflector 112 relative to cone 201). As the distance 121 between the near end of the reflector and the eye increases, so too must the length 122 of the reflector increase so as to map a substantial portion (or all) of the central field portion 115 onto the peripheral sensor portion. For a frusto-conical reflector having a near end about 25 mm (about 1 inch) from the eye and a near-end opening that just admits the macular cone angle 201, the reflector must be several inches long in order to map the entire central field portion 115 onto the peripheral retina portion. Mounting reflectors than long onto eyeglasses or a headset would be unwieldly.

To mitigate that reflector size issue, imagine a single frusto-conical or reflector 112 cut into multiple transverse slices 320 (FIG. 7) and collapsed onto a common, substantially flat mounting surface. To preserve the inverted mapping described above for a single cone, the cone angle of each slice would be adjusted by simple trigonometric calculation according to how far it is displaced by the "collapse." The resulting set of peripheral optical elements 320 would then resemble FIG. 8, in which the elements 320 (with reflective surfaces 323) are mounted on a substantially transparent substrate 322 and direct the rays 325 emanating from the central field portion 324 to form the mapping on the peripheral sensor portion. Alternatively, the cone angles can instead be adjusted to provide, e.g., a non-inverted mapping of the central image onto the peripheral sensor portion. The spacing 326 should be selected, by simple geometric calculation, to reduce to an acceptable level or minimize occlusion by one element 320 of rays 325 reflected by another element 320. The sampling of rays 325 by the reflective elements 320/323 need not be contiguous; it may be desirable, however, for the mapping provided by those reflective elements be substantially contiguous on the peripheral sensor portion. The resulting set of multiple nested frusto-conical reflector segments 320 can in some respects resemble a Fresnel lens. The nested elements can be substantially concentric in some examples, or may not be concentric in other examples. A single frusto-pyramidal reflector can be similarly "sliced" and "collapsed" and "pyramid-angle-adjusted" to provide a set of multiple nested frusto-pyramidal segments to act as the peripheral optical elements.

In the example of FIG. 9, the reflective peripheral optical elements include the prismatic reflectors with reflective faces 410 and transmissive faces 411. The prismatic reflectors are mounted on or formed on a substantially transparent substrate 402, which can comprise the same material 403 as the prismatic reflectors or a different material. The arrangement and performance of the prismatic reflectors can be substantially similar to those described above, with the rays 405 redirected by internal refection (total or not, depending on the incidence angles and the refractive index of material 403) from the reflective faces 410. In some examples normal incidence on the substrate 402 and the transmissive faces 411 results in no refractive redirection of the rays 405 emanating from the central field portion 404. In other examples, non-normal incidence on one or both of those surfaces results in refractive redirection of the rays 405 emanating from the central field portion 404.

In some examples, the set of one or more reflective optical elements includes a set of multiple substantially flat reflector facet segments generally arranged to provide a suitable mapping of the central image onto the peripheral sensor portion, including inverted or non-inverted radial outward displacement, one or more substantially rectilinear displacements (at least partly preserving relative distances or angles, with or without including overall magnification or demagnification), multiple mappings, or other suitable mapping arrangements.

In some examples, instead of or in addition to one or more reflective optical elements, the peripheral optical elements can include one or more refractive optical elements. The refractive elements can be arranged similarly to the reflective elements described above, including, e.g., frusto-conical (including variants described above, e.g., right or oblique; circular, elliptical, oval, or other; constant or varying angle; sliced/collapsed/nested/adjusted), frusto-pyramidal (including variants listed above, e.g., right or oblique; regular or irregular polygon; constant or varying slope; sliced/collapsed/nested/adjusted), or a set of multiple substantially flat prismatic facet segments. The set of one or more peripheral optical elements that includes one or more refractive optical elements can be arranged to produce mappings of the central image onto the peripheral sensor portion similar to those produced by the reflective elements described above (e.g., inverted, non-inverted, rectilinear, and so forth).

In the examples of FIGS. 10 and 11, the set of one or more peripheral optical elements includes one or more focusing optical elements 501/503 and one or more apertures 502. Rays 505 emanating from the central field portion 504 are relayed by the lenses 501/503 through the aperture 502 and onto the peripheral retina portion. In the example of FIG. 11, the rays 505 are further directed by a refractive optical element 506 (e.g., a prism in this example). In other examples, one or more reflective, refractive, or diffractive optical elements can be incorporated into arrangements that include one or more focusing elements and one or more apertures. The arrangements of FIGS. 10 and 11 can be well suited for producing one or more substantially rectilinear mappings of the central image onto the peripheral retina portion.

In the examples of FIGS. 13 and 14, the one or more peripheral optical elements include a pair a annular or ring-shaped reflectors 601 and 602 (only one side of each ring depicted in the figures). The outer reflector 601 redirects rays 600 emanating from the central field portion onto the inner reflector 602, which in turn redirects the rays onto the peripheral retina portion 607a/607b. The arrangements of FIGS. 13 and 14 results in an inverted mapping of the central image onto the peripheral retina portion 607I/607b. Instead of, or in addition to, one or more annular reflectors, in some examples the one or more peripheral optical elements can include an annular prism 615, as in the example of FIG. 15. Sizes, spacings, or orientations of the optical elements 601, 602, or 615 can be varied so as to effect a suitable or desired mapping of the central image onto the peripheral retina portion.

Instead of or in additional to any of the optical elements described above, in some examples the one or more peripheral optical elements can include one or more diffractive optical elements, e.g., one or more Fresnel lenses or diffractive beam deflectors.

In the specific examples shown, rays emanating from the central field portion and directed onto the peripheral sensor portion without crossing, before reaching the central optical elements, an "imaging axis" or "imaging center line" defined by the central sensor portion and the one or more central optical elements. There is no reason such a crossing, or multiple crossings, cannot be employed to achieve a desired mapping. For example, the examples of FIGS. 13 and 14 could be modified so that a ray 600 can be directed by reflector 601 on one side of the eye to a reflector 602 on the other side of the eye. Any suitable one or more directions or redirections of rays emanating from the central field portion, by the one or more peripheral optical elements, can be employed for conveying those rays onto the peripheral sensor portion via the one or more central optical elements.

In some examples the set of one or more peripheral optical elements further includes one or more wavelength-dependent optical filters, diffractive optical elements, or refractive optical elements. Such wavelength-dependent optical element can be arranged so as to direct the light emanating from the central field portion to different regions of the peripheral sensor portion according to wavelength.

A common arrangement for positioning the set of one or more peripheral optical elements relative to a user's eye and visual field is mounting the one or more peripheral optical elements on, or incorporating the peripheral optical elements into, a pair of eyeglasses, a piece of eyewear, a headset, a head-mounted display (for displaying the user's visual field), other similar item. In the example of FIG. 12, an arrangement of one or more peripheral optical elements 550 mounted on a pair of eyeglasses receive rays 551 from the central field portion and direct it onto the peripheral retina portion by reflection form a lens 552 of the eyeglasses. That arrangement can be well-suited for providing a substantially rectilinear mapping of the central image onto the peripheral retina portion. In the example of FIG. 16, the one or more peripheral optical elements are incorporated into the contact lens 711, which directs rays 700 from the central field portion onto the peripheral retina portion 707. In another example, at least a portion of the set of one or more peripheral optical elements is incorporated into an ocular implant.

In examples wherein the one or more peripheral optical elements are mounted in front of a user's eyes, e.g., with eyeglasses, eyewear, a headset, or a head-mounted display, alignment between the user's eyes and the one or more peripheral optical elements can be spoiled if the user moves his eyes to look up, down, or to one side or the other. If such misalignment occurs, some of the central image (as defined by the peripheral optical elements) might be imaged onto a portion of the peripheral retina portion, or a portion of the mapped central image might be directed to the central retina portion. The example of FIG. 16 does not suffer this problem, because the one or more peripheral optical elements move with the eye. An eye-tracking sensor and one or more actuators can be arranged in some examples so as to alter the arrangement of the one or more peripheral optical elements in response to eye movements detected by the eye-tracking sensor. The tracking sensor and actuators can act to maintain substantial alignment between the user's eyes and the one or more peripheral optical elements. Any suitable sensor or actuators can be employed. In some examples, angles of reflective or refractive elements can be altered in response to user eye movements; in some examples, an aperture can be translated in response to user eye movements; other suitable schemes can be implemented.

Figure 17:
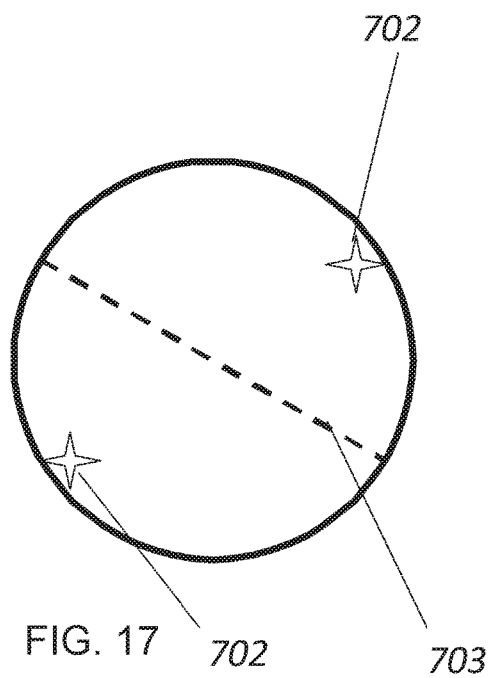
FIG. 17 illustrates schematically one or more visual cues directed to a peripheral retina portion to indicate a user's position, spatial orientation, or curvilinear or rotational movement.

In some examples, the apparatus includes one or more acceleration or rotation sensors and one or more optically emissive or attenuating elements (e.g., an LED or a liquid crystal spatial attenuator) operationally coupled to the one or more acceleration or rotation sensors. The sensors and emissive/attenuating elements can be operatively coupled so as so provide one or more visual cues (e.g., stars 702 or dashed line 703 in FIG. 17), directed to one or more corresponding segments of the peripheral retina portion, as to a user's position, orientation, or curvilinear or rotational movement. Repeated use of the apparatus by a person suffering from vertigo, for example, due to malfunctioning of the semicircular canals, can train her brain to focus on the provided visual cues to resolve sensory inconsistencies that cause the vertigo.

Figure 18:
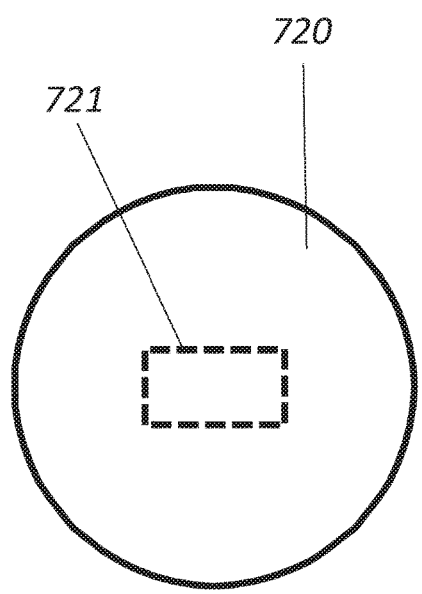
FIG. 18 illustrates schematically alternative projected positions of displayed content on central and peripheral retina portions.

In some examples, the apparatus is incorporated into a heads-up, augmented-reality, or virtual-reality display. The display and the set of one or more peripheral optical elements are arranged so as to project displayed content onto one or more corresponding segments of the peripheral retina portion 720, instead of central retinal portion 721 as is typically the case with such displays (FIG. 18).

In an example different from those described this far, the peripheral optical elements include image manipulation software and circuitry in a video display. The video display is structured and programmed so as to display its visual content in a central portion of the display (e.g., roughly coinciding with the viewer's macular visual field) and also display that central visual content mapped onto peripheral portions of the video display, according to any suitable mapping scheme (radial, rectilinear, inverted or not, and so on). If the viewer focuses on the center of the screen, the content mapped onto the peripheral portions of the screen will be imaged by the viewer's eyes onto the peripheral retina portion. The effect would be the same as if the viewer employed a set of one or more peripheral optical elements (e.g., on eyeglasses) and viewed a normal video display. If the viewer uses a portable version of the inventive optical apparatus (e.g., as eyeglasses), the same mapping scheme is preferably employed for both the video screen and the eyeglasses. The eyeglasses need not be worn while using the video display.

The inventive optical apparatus and methods disclosed herein can be advantageously employed for augmenting a user's normal vision under certain circumstances, including, e.g., when the user is engaged in hunting, combat training or maneuvers, or nighttime activities. By shifting visual content from the central field portion to the peripheral retina portion that is predominantly populated by rod photoreceptors, the user's night vision of the center of her visual field is enhanced. It has also been observed that transverse motion of an object across the user's central visual field is perceived, while using the inventive apparatus, as rapid movement toward or away from the user in his peripheral visual field. Human vision is much more sensitive to perceiving such apparent longitudinal motion than to perceiving transverse motion, and is generally more sensitive to perceiving motion in the peripheral visual field than in the central visual field. The effect is observed whether the peripheral retina portion extends into the macula or not, but the effect is further enhanced under low light conditions if the peripheral retina portion excludes the macula (e.g., is dominated by rod photoreceptors).

The inventive apparatus and methods disclosed herein can be advantageously employed for improving overall visual perception in patients with macular degeneration. As noted above, that condition degrades and eventually destroys visual reception in the macular region of the retina, but leaves the peripheral retina portion relatively unscathed. The inventive apparatus disclosed herein maps the central visual field portion onto functional peripheral portions of the retina, enabling the user to "see" his central visual field using his peripheral retina. A training period typically is required for a user to gain the full benefit of the inventive apparatus, particularly in the case of radial displacement mapping of the central field portion onto the peripheral retina portion (see, e.g., FIGS. 6A through 6C). However, the human brain's natural plasticity can be exploited, and after a training period a user can readily interpret her central visual field even though she only "sees" it in a distorted form mapped onto her peripheral retina portion. Such a user might also use the video display embodiment or the heads-up, virtual-reality, or augmented-reality display embodiments described above, for training or for normal use of such devices without the need for a separate apparatus (e.g., in the form of eyeglasses). The training can begin in the early stages of the user's macular vision loss. Viewing simultaneously the user's normal central visual field portion and the mapped version in his peripheral visual field, while not absolutely necessary, hastens development of the ability to properly interpret the mapped peripheral version as the normal central version gradually fades away over time.

The use of wavelength-dependent peripheral optical elements can in some examples enable the inventive apparatus to be employed to mitigate the effects of colorblindness. The central field portion can be mapped onto multiple different locations in the peripheral retina portion, each with different wavelength-dependent optical elements. The user's brain can be trained to associate visual information in different peripheral visual field regions as indicating different colors, even though the rod photoreceptors in those regions are not color sensitive.

It should be noted that light from an object field that is completely outside of the normal field of vision (such as behind the user) can be maneuvered by optics of the inventive apparatus to put the normally unseen onto the peripheral view of the user's eye.

In another example of a cross-sensory application of the inventive apparatus, a person suffering from pain sensor signals might be aided by a monitoring of muscle tension. As a result of a series of training cycles, the peripheral visual presentation in the presence of muscular tension from pain, could be that which the wearer has learned through a series of training cycles to associate with reduced pain or relaxation. The inventive apparatus in this general configuration also can be applicable to phantom limb pain, and other sensory deficiencies such as in taste or smell.

The inventive apparatus also can be used in the absence of, or reduction of, normal levels of other human sensory performance. For example, with the sudden onset of sleep for people with narcolepsy a simple device on the eyeglasses could sense an extended closure of a person's eyelids that suggests the eye can no longer see the road. Under that condition, a bright peripherally located light signal can be activated to awaken the person. Previous training cycles wherein the user has learned an automatic response to that signal, which is purposely differentiated from the bright lights of oncoming cars and street lamps, etc., will produce an awakening and possibly automatic performance of whatever response has been taught during the training program, e.g., such as pulling to the side of the road and stopping.

In addition to the preceding, the following examples fall within the scope of the present disclosure or appended claims:

Example 1

An optical apparatus comprising a set of one or more peripheral optical elements arranged so as to direct, onto a peripheral sensor portion of a visual sensor via a set of one or more central optical elements of the visual sensor, at least a portion of light emanating from a central field portion of a visual field so as to map at least a partial image of the central field portion onto the peripheral sensor portion for detection by the visual sensor, wherein the one or more central optical elements are arranged so as to define the central field portion and to form, from at least a portion of light emanating from the central field portion that would be directly incident on the one or more central optical elements, at least a partial image of the central field portion on a corresponding central sensor portion of the visual sensor that is distinct from the peripheral sensor portion.

Example 2

The optical apparatus of Example 1 wherein the visual sensor is a human eye of a user including a cornea, lens, and retina, the central sensor portion includes a central retina portion of the retina, the peripheral sensor portion includes a peripheral retina portion of the retina that surrounds the central retina portion, and the set of one or more central optical elements includes the cornea and the lens.

Example 3

The optical apparatus of Example 2 wherein the central retina portion includes predominantly cone photoreceptors and the peripheral retina portion includes predominantly rod photoreceptors.

Example 4

The optical apparatus of Example 2 wherein the central retina portion includes only a macular portion of the retina.

Example 5

The optical apparatus of Example 2 wherein the central retina portion includes only foveal and parafoveal portions of the retina.

Example 6

The optical apparatus of Example 2 wherein the central retina portion includes only a foveal portion of the retina.

Example 7

The optical apparatus of any one of Examples 2 through 6 wherein the set of one or more central optical elements further includes one or more corrective lenses.

Example 8

The optical apparatus of any one of Examples 2 through 7 wherein the set of one or more peripheral optical elements are mounted on or incorporated into pair of eyeglasses, a piece of eyewear, a headset, or a head-mounted display.

Example 9

The optical apparatus of any one of Examples 2 through 8 wherein at least a portion of the set of one or more peripheral optical elements is incorporated into a contact lens or an ocular implant.

Example 10

The optical apparatus of any one of Examples 2 through 9 further comprising a heads-up, augmented-reality, or virtual-reality display, wherein the display and the set of one or more peripheral optical elements are arranged so as to project displayed content onto one or more corresponding segments of the peripheral retina portion.

Example 11

The optical apparatus of any one of Examples 2 through 10 wherein the peripheral optical elements include image manipulation software and circuitry in a video display, wherein the video display is structured and programmed so as to map a central portion of displayed visual content onto peripheral portions of the video display, so that the mapped visual content is imaged on the peripheral retina portion.

Example 12

The optical apparatus of any one of Examples 2 through 11 further comprising an eye-tracking sensor and one or more actuators arranged so as to alter the arrangement of the one or more peripheral optical elements in response to eye movements detected by the eye-tracking sensor.

Example 13

The optical apparatus of any one of Examples 2 through 12 further comprising one or more acceleration or rotation sensors and one or more optically emissive or attenuating elements operationally coupled to the one or more acceleration or rotation sensors so as so provide one or more visual cues, directed to one or more corresponding segments of the peripheral retina portion, as to a user's position, spatial orientation, or curvilinear or rotational movement.

Example 14

The optical apparatus of any one of Examples 1 through 13 wherein the set of one or more peripheral optical elements is arranged so as to permit passage of at least a portion of the light to form the at least partial image of the central field portion on the corresponding central sensor portion.

Example 15

The optical apparatus of any one of Examples 1 through 14 wherein the set of one or more peripheral optical elements is arranged so as to define an image-mapping center point and so that the mapped at least partial image of the central field portion is mapped onto the peripheral sensor portion according to a non-inverted outward radial displacement relative to the center point, wherein a corresponding portion of the light emanating from each mapped segment of the central field portion is directed by one or more of the peripheral optical elements onto a corresponding segment of the peripheral sensor portion that is displaced, radially outward away from the center point, relative to a corresponding segment of the central sensor portion where that mapped central field portion would be imaged.

Example 16

The optical apparatus of any one of Examples 1 through 14 wherein the set of one or more peripheral optical elements is arranged so as to define an image-mapping center point and so that the mapped at least partial image of the central field portion is mapped onto the peripheral sensor portion according to an inverted outward radial displacement relative to the center point, wherein a corresponding portion of the light emanating from each mapped segment of the central field portion is directed by one or more of the peripheral optical elements onto a corresponding segment of the peripheral sensor portion that is displaced, radially outward across the center point, relative to a corresponding segment of the central sensor portion where that mapped central field portion would be imaged.

Example 17

The optical apparatus of any one of Examples 1 through 14 wherein the set of one or more peripheral optical elements is arranged so that the mapped at least partial image of the central field portion is mapped onto the peripheral sensor portion according to a substantially rectilinear displacement relative to the at least partial image of the central field portion formed on the central sensor portion.

Example 18

The optical apparatus of any one of Examples 1 through 17 wherein the set of one or more peripheral optical elements includes a set of one or more reflective optical elements.

Example 19

The optical apparatus of Example 18 wherein the set of one or more reflective optical elements includes a frusto-conical reflector, a set of multiple nested frusto-conical reflector segments, a frusto-pyramidal reflector, or a set of nested frusto-pyramidal reflectors.

Example 20

The optical apparatus of any one of Examples 18 or 19 wherein the set of one or more reflective optical elements includes a set of multiple substantially flat reflector facet segments.

Example 21

The optical apparatus of any one of Examples 18 through 20 wherein the set of one or more reflective optical elements includes one or more annular reflectors.

Example 22

The optical apparatus of any one of Examples 1 through 21 wherein the set of one or more peripheral optical elements includes a set of one or more refractive optical elements.

Example 23

The optical apparatus of Example 22 wherein the set of one or more refractive optical elements includes a frusto-conical prism or a set of multiple nested frusto-conical prismatic segments.

Example 24

The optical apparatus/method of any one of Examples 22 or 23 wherein the set of one or more refractive optical elements includes a set of multiple substantially flat prismatic facet segments.

Example 25

The optical apparatus of any one of Examples 22 through 24 wherein the set of one or more refractive optical elements includes one or more annular prisms.

Example 26

The optical apparatus of any one of Examples 1 through 25 wherein the set of one or more peripheral optical elements includes one or more focusing optical elements and one or more apertures.

Example 27

The optical apparatus of any one of Examples 1 through 26 wherein the set of one or more peripheral optical elements includes a set of one or more diffractive optical elements.

Example 28

The optical apparatus of any one of Examples 1 through 27 wherein the set of one or more peripheral optical elements further includes one or more wavelength-dependent optical filters, diffractive optical elements, or refractive optical elements, wherein said wavelength-dependent optical element are arranged so as to direct the light emanating from the central field portion to different regions of the peripheral sensor portion according to wavelength.

Example 29

A method performed using the optical apparatus of any one of Examples 1 through 28, the method comprising directing, using the set of one or more peripheral optical elements, onto the peripheral sensor portion of the visual sensor via the set of one or more central optical elements of the visual sensor, at least a portion of light emanating from the central field portion of the visual field so as to map at least a partial image of the central field portion onto the peripheral sensor portion for detection by the visual sensor.

Example 30

The method of Example 29 wherein the visual sensor is a human eye of a user including a cornea, lens, and retina, the central sensor portion includes a central retina portion of the retina, the peripheral sensor portion includes a peripheral retina portion of the retina that surrounds the central retina portion, and the set of one or more central optical elements includes the cornea and the lens.

Example 31

The method of Example 30 wherein the set of one or more peripheral optical elements are employed while the user is engaged in hunting, combat training or maneuvers, or nighttime activities, and mapping the at least partial image enhances the user's night vision or motion detection relative to the user's night vision or motion detection without employing the one or more peripheral optical elements.

Example 32

The method of Example 30 wherein the set of one or more peripheral optical elements are employed while the user's central visual field deteriorates due to macular degeneration, and the user's visual center adapts so as to interpret the at least partial image mapped onto the peripheral retina portion substantially the same as the at least partial image formed on the central retina portion in the absence of the macular degeneration.

It is intended that equivalents of the disclosed example embodiments and methods shall fall within the scope of the present disclosure or appended claims. It is intended that the disclosed example embodiments and methods, and equivalents thereof, may be modified while remaining within the scope of the present disclosure or appended claims.

In the foregoing Detailed Description, various features may be grouped together in several example embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed example embodiment. Thus, the appended claims are hereby incorporated into the Detailed Description, with each claim standing on its own as a separate disclosed embodiment. However, the present disclosure shall also be construed as implicitly disclosing any embodiment having any suitable set of one or more disclosed or claimed features (i.e., a set of features that are neither incompatible nor mutually exclusive) that appear in the present disclosure or the appended claims, including those sets that may not be explicitly disclosed herein. In addition, for purposes of disclosure, each of the appended dependent claims shall be construed as if written in multiple dependent form and dependent upon all preceding claims with which it is not inconsistent. It should be further noted that the scope of the appended claims does not necessarily encompass the whole of the subject matter disclosed herein.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open ended terminology, with the same meaning as if the phrase "at least" were appended after each instance thereof, unless explicitly stated otherwise. For purposes of the present disclosure or appended claims, when terms are employed such as "about equal to," "substantially equal to," "greater than about," "less than about," and so forth, in relation to a numerical quantity, standard conventions pertaining to measurement precision and significant digits shall apply, unless a differing interpretation is explicitly set forth. For null quantities described by phrases such as "substantially prevented," "substantially absent," "substantially eliminated," "about equal to zero," "negligible," and so forth, each such phrase shall denote the case wherein the quantity in question has been reduced or diminished to such an extent that, for practical purposes in the context of the intended operation or use of the disclosed or claimed apparatus or method, the overall behavior or performance of the apparatus or method does not differ from that which would have occurred had the null quantity in fact been completely removed, exactly equal to zero, or otherwise exactly nulled.

In the appended claims, any labelling of elements, steps, limitations, or other portions of a claim (e.g., first, second, etc., (a), (b), (c), etc., or (i), (ii), (iii), etc.) is only for purposes of clarity, and shall not be construed as implying any sort of ordering or precedence of the claim portions so labelled. If any such ordering or precedence is intended, it will be explicitly recited in the claim or, in some instances, it will be implicit or inherent based on the specific content of the claim. In the appended claims, if the provisions of 35 USC § 112(f) are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC § 112(f) are not intended to be invoked for that claim.

If any one or more disclosures are incorporated herein by reference and such incorporated disclosures conflict in part or whole with, or differ in scope from, the present disclosure, then to the extent of conflict, broader disclosure, or broader definition of terms, the present disclosure controls. If such incorporated disclosures conflict in part or whole with one another, then to the extent of conflict, the later-dated disclosure controls.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. An optical apparatus comprising a set of one or more peripheral optical elements arranged so as to direct, onto a peripheral sensor portion of a visual sensor via a set of one or more central optical elements of the visual sensor, at least a portion of light emanating from a central field portion of a visual field so as to map at least a partial image of the central field portion onto the peripheral sensor portion for detection by the visual sensor, wherein the one or more central optical elements are arranged so as to define the central field portion and to form, from at least a portion of light emanating from the central field portion that would be directly incident on the one or more central optical elements, at least a partial image of the central field portion on a corresponding central sensor portion of the visual sensor that is distinct from the peripheral sensor portion, wherein:

(a) the set of one or more peripheral optical elements is arranged so as to define an image-mapping center point and so that the mapped at least partial image of the central field portion is mapped onto the peripheral sensor portion according to a non-inverted outward radial displacement relative to the center point, wherein a corresponding portion of the light emanating from each mapped segment of the central field portion is directed by one or more of the peripheral optical elements onto a corresponding segment of the peripheral sensor portion that is displaced, radially outward away from the center point, relative to a corresponding segment of the central sensor portion where that mapped central field portion would be imaged;

(b) the set of one or more peripheral optical elements is arranged so as to define an image-mapping center point and so that the mapped at least partial image of the central field portion is mapped onto the peripheral sensor portion according to an inverted outward radial displacement relative to the center point, wherein a corresponding portion of the light emanating from each mapped segment of the central field portion is directed by one or more of the peripheral optical elements onto a corresponding segment of the peripheral sensor portion that is displaced, radially outward across the center point, relative to a corresponding segment of the central sensor portion where that mapped central field portion would be imaged; or (c) the set of one or more peripheral optical elements includes one or more of a frusto-conical reflector or refractor, a set of multiple nested frusto-conical reflector or refractor segments, a frusto-pyramidal reflector or refractor, or a set of nested frusto-pyramidal reflectors or refractors.

2. The optical apparatus of claim 1 wherein the visual sensor is a human eye of a user including a cornea, lens, and retina, the central sensor portion includes a central retina portion of the retina, the peripheral sensor portion includes a peripheral retina portion of the retina that surrounds the central retina portion, and the set of one or more central optical elements includes the cornea and the lens.

3. The optical apparatus of claim 2 wherein the central retina portion includes predominantly cone photoreceptors and the peripheral retina portion includes predominantly rod photoreceptors.

4. The optical apparatus of claim 2 wherein the central retina portion includes only a macular portion of the retina.

5. The optical apparatus of claim 2 wherein the central retina portion includes only a foveal portion of the retina.

6. The optical apparatus of claim 2 wherein the set of one or more peripheral optical elements are mounted on or incorporated into pair of eyeglasses, a piece of eyewear, a headset, or a head-mounted display.

7. The optical apparatus of claim 2 further comprising an eye-tracking sensor and one or more actuators arranged so as to alter the arrangement of the one or more peripheral optical elements in response to eye movements detected by the eye-tracking sensor.

8. The optical apparatus of claim 2 wherein the peripheral optical elements include image manipulation software and circuitry in a video display, wherein the video display is structured and programmed so as to map a central portion of displayed visual content onto peripheral portions of the video display, so that the mapped visual content is imaged on the peripheral retina portion.

9. The optical apparatus of claim 2 wherein at least a portion of the set of one or more peripheral optical elements is incorporated into a contact lens or an ocular implant.

10. The optical apparatus of claim 2 further comprising one or more acceleration or rotation sensors and one or more optically emissive or attenuating elements operationally coupled to the one or more acceleration or rotation sensors so as so provide one or more visual cues, directed to one or more corresponding segments of the peripheral retina portion, as to a user's position, spatial orientation, or curvilinear or rotational movement.

11. The optical apparatus of claim 2 further comprising a heads-up, augmented-reality, or virtual-reality display, wherein the display and the set of one or more peripheral optical elements are arranged so as to project displayed content onto one or more corresponding segments of the peripheral retina portion.

12. The optical apparatus of claim 1 wherein the set of one or more peripheral optical elements is arranged so as to permit passage of at least a portion of the light to form the at least partial image of the central field portion on the corresponding central sensor portion.

13. The optical apparatus of claim 1 wherein the set of one or more peripheral optical elements is arranged so as to define an image-mapping center point and so that the mapped at least partial image of the central field portion is mapped onto the peripheral sensor portion according to a non-inverted outward radial displacement relative to the center point, wherein a corresponding portion of the light emanating from each mapped segment of the central field portion is directed by one or more of the peripheral optical elements onto a corresponding segment of the peripheral sensor portion that is displaced, radially outward away from the center point, relative to a corresponding segment of the central sensor portion where that mapped central field portion would be imaged.

14. The optical apparatus of claim 1 wherein the set of one or more peripheral optical elements is arranged so as to define an image-mapping center point and so that the mapped at least partial image of the central field portion is mapped onto the peripheral sensor portion according to an inverted outward radial displacement relative to the center point, wherein a corresponding portion of the light emanating from each mapped segment of the central field portion is directed by one or more of the peripheral optical elements onto a corresponding segment of the peripheral sensor portion that is displaced, radially outward across the center point, relative to a corresponding segment of the central sensor portion where that mapped central field portion would be imaged.

15. The optical apparatus of claim 1 wherein the set of one or more peripheral optical elements is arranged so that the mapped at least partial image of the central field portion is mapped onto the peripheral sensor portion according to a substantially rectilinear displacement relative to the at least partial image of the central field portion formed on the central sensor portion.

16. The optical apparatus of claim 1 wherein the set of one or more refractive optical elements includes one or more substantially flat reflector facet segments or one or more substantially flat prismatic facet segments.

17. The optical apparatus of claim 1 wherein the set of one or more peripheral optical elements includes one or more of a frusto-conical reflector or refractor, a set of multiple nested frusto-conical reflector or refractor segments, a frusto-pyramidal reflector or refractor, or a set of nested frusto-pyramidal reflectors or refractors.

18. The optical apparatus of claim 1 wherein the set of one or more peripheral optical elements includes one or more annular optical elements.

19. The optical apparatus of claim 1 wherein the set of one or more peripheral optical elements includes one or more focusing optical elements and one or more apertures.

20. The optical apparatus of claim 1 wherein the set of one or more peripheral optical elements includes one or more diffractive optical elements.

21. The optical apparatus of claim 1 wherein the set of one or more peripheral optical elements includes one or more wavelength-dependent optical filters, diffractive optical elements, or refractive optical elements, wherein said wavelength-dependent optical element are arranged so as to direct the light emanating from the central field portion to different regions of the peripheral sensor portion according to wavelength.

22. A method for using the optical apparatus of claim 1, the method comprising directing, using the set of one or more peripheral optical elements, onto the peripheral sensor portion of the visual sensor via the set of one or more central optical elements of the visual sensor, at least a portion of light emanating from a central field portion of a visual field so as to map at least a partial image of the central field portion onto the peripheral sensor portion for detection by the visual sensor.

23. The method of claim 22 wherein the visual sensor is a human eye of a user including a cornea, lens, and retina, the central sensor portion includes a central retina portion of the retina, the peripheral sensor portion includes a peripheral retina portion of the retina that surrounds the central retina portion, and the set of one or more central optical elements includes the cornea and the lens.

24. The method of claim 23 wherein the set of one or more peripheral optical elements are employed while the user is engaged in hunting, combat training or maneuvers, or nighttime activities, and mapping the at least partial image enhances the user's night vision or motion detection relative to the user's night vision or motion detection without employing the one or more peripheral optical elements.

25. The method of claim 23 wherein the set of one or more peripheral optical elements are employed while the user's central visual field deteriorates due to macular degeneration, and the user's visual center adapts so as to interpret the at least partial image mapped onto the peripheral retina portion substantially the same as the at least partial image formed on the central retina portion in the absence of the macular degeneration.

* * * * *